United States Patent [19]

Cozzi et al.

[11] Patent Number: 5,356,920
[45] Date of Patent: Oct. 18, 1994

[54] IMIDAZOL-2-YL DERIVATIVES OF SUBSTITUTED BICYCLIC COMPOUNDS

[75] Inventors: Paolo Cozzi; Daniele Fancelli; Severino Dino, all of Milan; Augusto Chiari, Florence; Giancarlo Ghiselli, Busto Arsizio, all of Italy

[73] Assignee: Farmitalia Carlo Erba SRL., Milan, Italy

[21] Appl. No.: 915,835

[22] PCT Filed: Nov. 26, 1991

[86] PCT No.: PCT/EP91/02228
  § 371 Date: Jul. 24, 1992
  § 102(e) Date: Jul. 24, 1992

[87] PCT Pub. No.: WO89/08646
  PCT Pub. Date: Sep. 21, 1989

[30] Foreign Application Priority Data

Nov. 28, 1990 [GB] United Kingdom ............ 9025848

[51] Int. Cl.⁵ .............. A61K 31/415; C07D 405/02; C07D 233/60
[52] U.S. Cl. .......................... 514/397; 514/399; 548/311.4; 548/338.1; 548/341.1; 548/341.5
[58] Field of Search ........... 548/311.4, 338.1, 341.1, 548/341.5; 514/397, 399

[56] References Cited

U.S. PATENT DOCUMENTS 4,510,149 4/1985 Cozzi et al. .............. 548/311.4
4,985,440 1/1991 Cozzi et al. .............. 548/311.4

Primary Examiner—Patricia L. Morris
Attorney, Agent, or Firm—Nikaido Marmelstein Murray & Oram

[57] ABSTRACT

Compounds having formula (I)

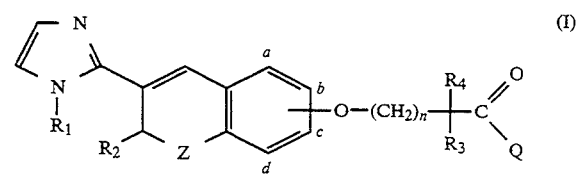

wherein Z is —O— or —$CH_2$—; n is 1-6; R is hydrogen, $C_1$-$C_6$ alkyl, phenyl or optionally substituted phenyl-$C_1$-$C_3$ alkyl; $R_2$ is $C_1$-$C_8$-alkyl, aryl-$C_1$-$C_3$ alkyl, $C_5$-$C_8$ cycloalkyl or $C_5$-$C_8$ cycloalkyl-$C_1$-$C_3$ alkyl; each of $R_3$ and $R_4$ independently is hydrogen or $C_1$-$C_4$ alkyl, or taken together with the carbon atom to which they are linked form a $C_3$-$C_6$ cycloalkyl ring; Q is —OR' or —NR'R" in which R' and R" are as herein defined, or Q is $C_1$-$C_8$ alkyl, phenyl, phenyl-$C_1$-$C_3$-alkyl, $C_5$-$C_8$ cycloalkyl or $C_5$-$C_8$ cycloalkyl-$C_1$-$C_3$ alkyl, in which both the phenyl and cycloalkyl rings or moieties are optionally substituted as herein defined; and the pharmaceutically acceptable salts thereof; are useful in particular as antidislipidaemic and antiatherosclerotic agents.

4 Claims, No Drawings

IMIDAZOL-2-YL DERIVATIVES OF SUBSTITUTED BICYCLIC COMPOUNDS

The present invention relates to new imidazol-2-yl derivatives of bicyclic compounds, in particular to imidazol-2-yl derivatives of 2H-1-benzopyran and 1,2-dihydronaphthalene, to a process for their preparation and to pharmaceutical compositions containing them.

WO-A-89/08646 discloses imidazol-2-yl derivatives having related chemical structure and analogous biological activity. However the compounds according to the present invention are more active than said prior-art compounds as shown by the comparative test data herein reported.

The invention provides compounds having the following general formula (I)

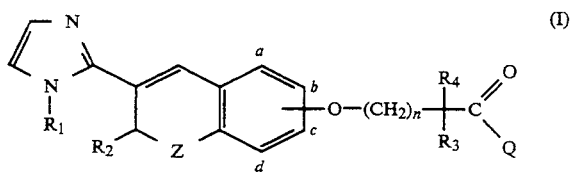

wherein
Z is —O— or —CH$_2$—;
n is an integer of 1 to 6;
R$_1$ is hydrogen, C$_1$–C$_6$ alkyl or a phenyl or phenyl-C$_1$–C$_3$ alkyl group wherein the phenyl ring is unsubstituted or substituted by a substituent chosen from halogen, C$_1$–C$_4$ alkyl and trihalo-C$_1$–C$_4$ alkyl;
R$_2$ is a) C$_1$–C$_8$ alkyl; b) an aryl-C$_1$–C$_3$ alkyl group wherein the aryl moiety is unsubstituted or substituted by one to three substitutents chosen independently from C$_1$–C$_4$ alkyl, halogen and trihalo-C$_1$–C$_4$ alkyl; or c) a C$_5$–C$_8$ cycloalkyl or C$_5$–C$_8$ cycloalkyl-C$_1$–C$_3$ alkyl group wherein the cycloalkyl ring is optionally substituted by one or two C$_1$–C$_4$ alkyl groups, which may be the same or different;
each of R$_3$ and R$_4$ independently is hydrogen or C$_1$–C$_4$ alkyl, or taken together with the carbon atom to which they are linked form a C$_3$–C$_6$ cycloalkyl ring;
Q is
a') C$_1$–C$_8$ alkyl;
b') —OR' in. which R' is hydrogen or C$_1$–C$_8$ alkyl;
c')

wherein each of R' and R" independently is hydrogen or C$_1$–C$_8$ alkyl, or one is hydrogen or C$_1$–C$_8$ alkyl and the other is a") a C$_5$–C$_8$ cycloalkyl ring unsubstituted or substituted by 1, 2 or 3 C$_1$–C$_4$ alkyl groups, which may be the same or different; or b") a phenyl ring unsubstituted or substituted by 1 to 3 substitutents independently chosen from C$_1$–C$_4$ alkyl, C$_1$–C$_4$ alkoxy, halogen and trihalo-C$_1$–C$_4$ alkyl;
d') a phenyl or phenyl-C$_1$–C$_3$ alkyl group wherein the phenyl ring is unsubstituted or substituted by 1 to 3 substituents independently chosen from C$_1$–C$_4$ alkyl, C$_1$–C$_4$ alkoxy, halogen and trihalo-C$_1$–C$_4$ alkyl; or
e') a C$_5$–C$_8$ cycloalkyl or C$_5$–C$_8$ cycloalkyl-C$_1$–C$_3$ alkyl group wherein the cycloalkyl ring is unsubstituted or substituted by one or two C$_1$–C$_4$ alkyl groups, which may be the same or different; and the pharmaceutically acceptable salts thereof, and wherein, when at the same time Q is —OR' in which R' is hydrogen or C$_1$–C$_4$ alkyl, R$_1$ is hydrogen or C$_1$–C$_6$ alkyl, R$_2$ is C$_1$–C$_8$ alkyl, R$_4$ is hydrogen or C$_1$–C$_4$ alkyl and n is an integer of 1 to 3, then R$_3$, being as defined above, is other than methyl.

The above proviso excludes from the scope of the compounds of formula (I) the prior art compounds disclosed in WO-A-89/08646.

The invention also includes within its scope all the possible isomers, stereoisomers and their mixtures and the metabolites and the metabolic precursors or bio-precursors of the compounds of formula (I). Pharmaceutically acceptable salts of the compounds of formula (I) include acid addition salts, with inorganic, e.g. nitric, hydrochloric, hydrobromic, sulphuric, perchloric and phosphoric acids, or organic, e.g. acetic, propionic, glycolic, lactic, oxalic, malonic, malic, maleic, tartaric, citric, benzoic, cinnamic, mandelic, fumaric, methanesulfonic and salicylic acids, and salts with inorganic, e.g. alkali metal, especially sodium or potassium, bases or alkaline-earth metal, especially calcium or magnesium, or with organic bases, e.g. alkylamines, preferably triethylamine, or basic naturally occurring aminoacids, preferably arginine. The alkyl groups may be branched or straight chain groups. A C$_1$–C$_8$ alkyl group is e.g. a C$_1$–C$_6$ alkyl group, in particular methyl, propyl, butyl or hexyl.

A C$_1$–C$_4$ alkyl group is preferably methyl, ethyl, propyl, isopropyl or butyl, in particular methyl, ethyl or isopropyl. A C$_1$–C$_4$ alkoxy group is preferably methoxy, ethoxy, propoxy or isopropoxy, in particular methoxy or ethoxy. A halogen atom is e.g. chlorine, bromine or fluorine, in particular chlorine or fluorine.

A trihalo-C$_1$–C$_4$ alkyl group is e.g. a trichloro- or trifluoro-C$_1$–C$_4$ alkyl group, in particular trifluoromethyl. A phenyl-C$_1$–C$_3$ alkyl group is e.g. benzyl or phenylethyl, in particular benzyl.

The aryl moiety in an aryl-C$_1$–C$_3$ alkyl group may be both, e.g. a phenyl or naphthyl, in particular phenyl, ring and a heteromonocyclic ring. Said heteromonocyclic ring may contain from 1 to 3 heteroatoms independently chosen from nitrogen, sulfur and oxygen; and preferably it is a thienyl or pyridyl ring, in particular 2- or 3-pyridyl or 2- or 3-thienyl. A C$_5$–C$_8$ cycloalkyl group or a cycloalkyl moiety in a C$_5$–C$_8$ cycloalkyl-C$_1$–C$_3$alkyl group is e.g. a cyclopentyl or a cyclohexyl ring. A C$_5$–C$_8$ cycloalkyl-C$_1$–C$_3$ alkyl group is preferably a C$_5$–C$_8$ cycloalkyl-methyl or C$_5$–C$_8$ cycloalkyl-ethyl group, in particular cyclopentyl-methyl and cyclohexyl-methyl.

A C$_3$–C$_6$ cycloalkyl ring is e.g. a cyclopropyl, cyclopentyl or cyclohexyl ring, in particular a cyclopentyl or cyclohexyl one. The —(CH$_2$)$_n$-chain, when n is higher than 1, may be a branched or straight alkylene chain. The substituent —O—(CH$_2$)$_n$—C(R$_3$R$_4$)—C(O)Q in which n, R$_3$, R$_4$ and Q are as defined above may be attached to any of the positions a to d on the benzene moiety, the position b and c being the preferred.

As stated above, the present invention includes within its scope also the pharmaceutically acceptable bio-precursors (otherwise known as pro-drugs) of the compounds of formula (I), i.e. compounds which have a different formula to formula (I) above, but which nevertheless upon administration to a human being are converted directly or indirectly in vivo into a compound of formula (I). Preferred compounds of the invention are the compounds of formula (I), wherein Z is —O— or —CH$_2$—;
n is an integer of 3 to 6;
R$_1$ is hydrogen or C$_1$–C$_4$ alkyl;
R$_2$ is a C$_3$–C$_6$ alkyl or aryl-C$_1$–C$_3$ alkyl group, wherein the aryl moiety is unsubstituted or substituted by a substituent chosen from halogen, C$_1$–C$_4$ alkyl and trifluoromethyl;
each of R$_3$ and R$_4$, which may be the same or different, is C$_1$–C$_4$ alkyl or, taken together with the carbon atom to which they are linked, they form a cyclopentyl or cyclohexyl ring;
Q is
a) C$_1$–C$_6$ alkyl;
b)

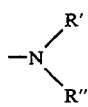

wherein one of R' and R" is hydrogen and the other is a') hydrogen, b') C$_4$–C$_8$ alkyl, c') a C$_5$–C$_8$ cycloalkyl ring unsubstituted or substituted by 1, 2 or 3 C$_1$–C$_4$ alkyl groups, which may be the same or different, or d') a phenyl ring unsubstituted or substituted by 1, 2 or 3 substituents independently chosen from C$_1$–C$_4$ alkyl, C$_1$–C$_4$ alkoxy, halogen and trifluoromethyl;

c) a phenyl or phenylmethyl group, wherein the phenyl ring is unsubstituted or substituted by 1, 2 or 3 substituents independently chosen from C$_1$–C$_4$ alkyl, C$_1$–C$_4$ alkoxy, halogen and trifluoromethyl; or d) a cyclohexyl or cyclohexylmethyl group, wherein the cycloalkyl ring is unsubstituted or substituted by one or two C$_1$–C$_4$ alkyl groups, which may be the same or different; and the pharmaceutically acceptable salts thereof.

Examples of preferred compounds of the invention are the following:

1. ethyl 5-[2-benzyl-3-(1-methyl-1H-imidazol-2-yl)-2H-1-benzopyran-6-yl]oxy-2,2-dimethylpentanoate;
2. ethyl 5-[2-(2-phenylethyl)-3-(1-methyl-1H-imidazol-2-yl)-2H-1-benzopyran-6-yl]oxy-2,2-dimethylpentanoate;
3. isopropyl 5-[2-(2-phenylethyl)-3-(1-methyl-1H-imidazol-2-yl)-2H-1-benzopyran-6-yl]oxy-2,2-dimethylpentanoate;
4. ethyl 5-[2-(2-(4-fluorophenyl)ethyl)-3-(1-methyl-1H-imidazol-2-yl)-2H-1-benzopyran-6-yl]oxy-2,2-dimethylpentanoate;
5. ethyl 1-[3-(2-(2-phenylethyl)-3-(1-methyl-1H-imidazol-2-yl)-2H-1-benzopyran-6-yl)oxypropyl]-cyclopentane-1-carboxylate;
6. ethyl 5-[2-(2-phenylethyl)-3-(1-methyl-1H-imidazol-2-yl)-2H-1-benzopyran-7-yl]oxy-2,2-dimethylpentanoate;
7. 5-[2-(2-(4-fluorophenyl)ethyl)-3-(1-methyl-1H-imidazol-2-yl)-2H-1-benzopyran-6-yl]oxy-2,2-dimethyl-N-isobutylpentanamide;
8. 5-[2-(2-phenylethyl)-3-(1-methyl-1H-imidazol-2-yl)-2H-1-benzopyran-6-yl]oxy-2,2-dimethyl-N-cyclohexylpentanamide;
9. 5-[2-(2-phenylethyl)-3-(1-methyl-1H-imidazol-2-yl)-2H-1-benzopyran-6-yl]oxy-2,2-dimethyl-N-(2,4-dimethoxy-phenyl)pentanamide;
10. 5-[2-(2-phenylethyl)-3-(1-methyl-1H-imidazol-2-yl)-2H-1-benzopyran-6-yl]oxy-2,2-dimethyl-N-(2,4,6-trifluorophenyl)pentanamide;
11. 5-[2-(2-phenylethyl)-3-(1-methyl-1H-imidazol-2-yl)-2H-1-benzopyran-6-yl]oxy-2,2-dimethyl-N-(2,4,6-trimethoxyphenyl)pentanamide;
12. 5-[2-(2-phenylethyl)-3-(1-methyl-1H-imidazol-2-yl)-2H-1-benzopyran-6-yl]oxy-2,2-dimethyl-N-(2,6-diisopropylphenyl)pentanamide;
13. 5-[2-(2-(4-fluorophenyl)ethyl)-3-(1-methyl-1H-imidazol-2-yl)-2H-1-benzopyran-6-yl]oxy-2,2-dimethyl-N-(2,6-diisopropylphenyl)pentanamide;
14. 5-[2-(2-(2,4-difluorophenyl)ethyl)-3-(1-methyl-1H-imidazol-2-yl)-2H-1-benzopyran-6-yl]oxy-2,2-dimethyl-N-(2,4-dimethoxyphenyl)pentanamide;
15. 5-[2-(2-(4-fluorophenyl)ethyl)-3-(1-methyl-1H-imidazol-2-yl)-2H-1-benzopyran-6-yl]oxy-2,2-dimethyl-N-cyclohexylpentanamide;
16. 1-[3-[2-(2-phenylethyl)-3-(1-methyl-1H-imidazol-2-yl)-2H-1-benzopyran-6-yl]oxypropyl]cyclopentane-1-(N-2,6-diisopropylphenyl)carboxamide;
17. 1-[3-[2-(2-phenylethyl)-3-(1-methyl-1H-imidazol-2-yl)-2H-1-benzopyran-6-yl]oxypropyl]cyclopentane-1-N-cyclohexylcarboxamide;
18. 1-[3-[2-(2-(2,4-difluorophenyl)ethyl)-3-(1-methyl-1H-imidazol-2-yl)-2H-1-benzopyran-6-yl]oxypropyl]cyclopentane-1-N-(2,6-diisopropylphenyl)-carboxamide;
19. 5-[2-(2-(2,4-difluorophenyl)ethyl)-3-(1-methyl-1H-imidazol-2-yl)-2H-1-benzopyran-6-yl]oxy-2,2-dimethyl-N-(2,6-diisopropylphenyl)pentanamide;
20. 5-[2-(2-(4-fluorophenyl)ethyl)-3-(1-methyl-1H-imidazol-2-yl)-2H-1-benzopyran-6-yl]oxy-2,2-dimethyl-N-(2,4-dimethoxyphenyl)pentanamide;
21. 6-(4,4-dimethyl-5-oxooctyl)oxy-2-propyl-3-(1-methyl-1H-imidazol-2-yl)-2H-1-benzopyran;
22. 6-(4,4-dimethyl-5-oxooctyl)oxy-2-(2-phenylethyl)-3-(1-methyl-1H-imidazol-2-yl)-2H-1-benzopyran;
23. 6-(4,4-dimethyl-6-cyclohexyl-5-oxohexyl)oxy-2-(2-phenylethyl)-3-(1-methyl-1H-imidazol-2-yl)-2H-1-benzopyran; and
24. methyl 5-[2-(2-(2,4-difluorophenyl)ethyl)-3-(1-methyl-1H-imidazol-2-yl)-2H-1-benzopyran-6-yl]oxy-2,2-dimethylpentanoate, either as a single isomer or as a mixture of isomers thereof; and the pharmaceutically acceptable salts thereof.

The structural formulae of the above numbered compounds, indicated according to their progressive number, are reported in the following Table:

| Comp | Z | R$_1$ | R$_2$ | n | Substit. Position | R$_3$ | R$_4$ | Q |
|---|---|---|---|---|---|---|---|---|
| 1 | O | CH$_3$ | PhCH$_2$ | 3 | b | CH$_3$ | CH$_3$ | OEt |
| 2 | O | CH$_3$ | PhCH$_2$CH$_2$ | 3 | b | CH$_3$ | CH$_3$ | OEt |

-continued

| Comp | Z | R$_1$ | R$_2$ | n | Substit. Position | R$_3$ | R$_4$ | Q |
|---|---|---|---|---|---|---|---|---|
| 3  | 0 | CH$_3$ | PhCH$_2$CH$_2$ | 3 | b | CH$_3$ | CH$_3$ | OiPr |
| 4  | 0 | CH$_3$ | (4F)PhCH$_2$CH$_2$ | 3 | b | CH$_3$ | CH$_3$ | OEt |
| 5  | 0 | CH$_3$ | PhCH$_2$CH$_2$ | 3 | b | —(CH$_2$)$_4$— | | OEt |
| 6  | 0 | CH$_3$ | PhCH$_2$CH$_2$ | 3 | c | CH$_3$ | CH$_3$ | OEt |
| 7  | 0 | CH$_3$ | (4F)PhCH$_2$CH$_2$ | 3 | b | CH$_3$ | CH$_3$ | NHiBu |
| 8  | 0 | CH$_3$ | PhCH$_2$CH$_2$ | 3 | b | CH$_3$ | CH$_3$ | NHcycloHex |
| 9  | 0 | CH$_3$ | PhCH$_2$CH$_2$ | 3 | b | CH$_3$ | CH$_3$ | NH(2,4MeO)Ph |
| 10 | 0 | CH$_3$ | PhCH$_2$CH$_2$ | 3 | b | CH$_3$ | CH$_3$ | NH(2,4,6F)Ph |
| 11 | 0 | CH$_3$ | PhCH$_2$CH$_2$ | 3 | b | CH$_3$ | CH$_3$ | NH(2,4,6MeO)Ph |
| 12 | 0 | CH$_3$ | PhCH$_2$CH$_2$ | 3 | b | CH$_3$ | CH$_3$ | NH(2,6iPr)Ph |
| 13 | 0 | CH$_3$ | (4F)PhCH$_2$CH$_2$ | 3 | b | CH$_3$ | CH$_3$ | NH(2,6iPr)Ph |
| 14 | 0 | CH$_3$ | (2,4F)PhCH$_2$CH$_2$ | 3 | b | CH$_3$ | CH$_3$ | NH(2,4MeO)Ph |
| 15 | 0 | CH$_3$ | (4F)PhCH$_2$CH$_2$ | 3 | b | CH$_3$ | CH$_3$ | NHcycloHex |
| 16 | 0 | CH$_3$ | PhCH$_2$CH$_2$ | 3 | b | —(CH$_2$)$_4$— | | NH(2,6iPr)Ph |
| 17 | 0 | CH$_3$ | PhCH$_2$CH$_2$ | 3 | b | —(CH$_2$)$_4$— | | NHcycloHex |
| 18 | 0 | CH$_3$ | (2,4F)PhCH$_2$CH$_2$ | 3 | c | —(CH$_2$)$_4$— | | NH(2,6iPr)Ph |
| 19 | 0 | CH$_3$ | (2,4F)PhCH$_2$CH$_2$ | 3 | b | CH$_3$ | CH$_3$ | NH(2,6iPr)Ph |
| 20 | 0 | CH$_3$ | (4F)PhCH$_2$CH$_2$ | 3 | b | CH$_3$ | CH$_3$ | NH(2,6iMe)Ph |
| 21 | 0 | Pr | Pr | 3 | b | CH$_3$ | CH$_3$ | Pr |
| 22 | 0 | CH$_3$ | PhCH$_2$CH$_2$ | 3 | b | CH$_3$ | CH$_3$ | Pr |
| 23 | 0 | CH$_3$ | PhCH$_2$CH$_2$ | 3 | b | CH$_3$ | CH$_3$ | CH$_2$-cycloHex |
| 24 | 0 | CH$_3$ | (2,4F)PhCH$_2$CH$_2$ | 3 | b | CH$_3$ | CH$_3$ | OMe |

The abbreviations Me, Et, Pr, iPr, iBu, Hex and Ph mean Methyl, Ethyl, Propyl, Isopropyl, Isobutyl, Hexyl and Phenyl, respectively.

The compounds of the invention and the salts thereof can be obtained by a process comprising
a) reacting a compound of formula (II)

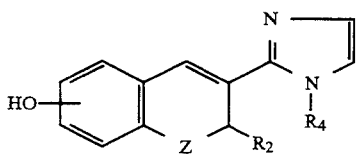
(II)

wherein Z, R$_1$ and R$_2$ are as defined above, with a compound of formula (III)

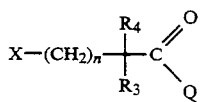
(III)

wherein X is a halogen atom or the residue of an active ester group and R$_3$, R$_4$, Q and n are as defined above; and if desired converting a compound of formula (I) into another compound of formula (I), and/or, if desired, converting a compound of formula (I) into a salt thereof, and/or, if desired, converting a salt into a free compound, and/or, if desired, resolving a mixture of isomers of compounds of formula (I) into the single isomers.

When X, in a compound of formula (III), is a halogen atom it is e.g. chlorine or bromine.

When X is the residue of an active ester, it is e.g. a mesyl or tosyl group, preferably a tosyl group.

The reaction of a compound of formula (II) with a compound of formula (III) may be carried out according to well known methods, in the presence of a suitable basic agent, in a suitable organic solvent; preferably with potassium tert.butoxide in tert.butanol or with anhydrous K$_2$CO$_3$ in acetone or with sodium hydride in dimethylformamide. The reaction may be performed at temperatures ranging from room temperature to reflux. The optional conversion of a compound of formula (I) into another compound of formula (I) may be carried out by methods known in themselves.

Thus, for example, a compound of formula (I) containing an esterified carboxy group may be converted into a compound of formula (I) containing a free carboxy group, by acidic or alkaline hydrolysis, operating at temperatures ranging from room temperature to about 100° C.

A compound of formula (I) containing a free carboxy group may be converted into a compound of formula (I) containing an esterified carboxy group by esterification, e.g. via the corresponding acid halide, e.g. chloride, or via a mixed anhydride, by reaction with an excess of a suitable C$_1$-C$_4$ alkyl alcohol, or by direct esterification, that is by reacting with the appropriate C$_1$-C$_4$ alcohol in the presence of an acidic catalyst, e.g. dry HCL or BF$_3$-etherate or SOCL$_2$.

The amides of formula (I) can be prepared e.g. from the acid chlorides by reaction of the latter with the desired amine in an aprotic solvent such as chloroform in the presence, if desired, of an acid scavenger such as triethylamine; alternatively, the acid themselves may be condensed with the desired amine in the presence of a suitable coupling reagent such as dicyclohexylcarbodiimide.

The optional salification of a compound of the invention as well as the separation of a mixture of isomers of a compound of the invention into the single isomers can be carried out according to well known methods in the art.

The compounds of formula (II) and Z, A, R$_2$ and R$_3$ are as defined above, may be obtained by a β-elimination reaction on a compound of formula (IV)

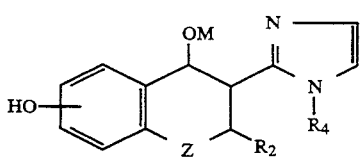
(IV)

wherein Z, R$_1$ and R$_2$ are as defined above and M represents hydrogen or an acyl group, in particular an acetyl group. The reaction may be performed in the presence of a suitable solvent, such as, glacial acetic acid, mixtures of acetic anhydride-pyridine, dimethylformamide (DMF) of dimethylsulfoxide (DMSO), or benzene, in the presence of suitable amounts, even catalytic amounts, of a strong acid, e.g., concentrated H₂SO₄, HCl, or p-toluenesulphonic acid, at temperatures ranging from about 50° C. to the reflux temperature. The same conversion may also be performed by refluxing a compound of formula (IV) in concentrated acids, e.g. hydrochloric or hydrobromic acid. When in a compound of formula (IV) M is an acyl group, in particular, acetyl, the reaction may also be carried out by pyrolysis, at temperatures ranging, typically, from about 200° C. to about 300° C.

The compounds of formula (III) are known compounds. The compounds of formula (IV) in which M represents hydrogen and Z, A, R₂ and R₃ are as defined above, may be obtained, e.g. by reducing a compound of formula (V)

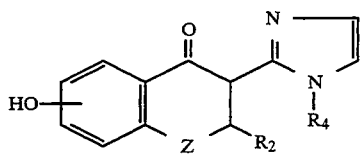

wherein Z, R₁ and R₂ are as defined above. The reduction may be performed according to well known procedures, for example, by treatment with an alkali metal borohydride, e.g. NaBH₄, in a suitable solvent, e.g. methyl or ethyl alcohol or a mixture of water and ethyl alcohol, or by treatment with LiAlH₄ in an anhydrous solvent, e.g. diethyl ether or tetrahydrofuran, at a temperature typically ranging in both cases from 0° C. to the reflux temperature, for reaction times varying approximately from 1 to 6 hours.

The compounds of formula (IV) wherein M is an acyl group may be obtained, for example, by reacting the corresponding compounds of formula (IV), in which M is hydrogen, with a suitable acyl halide, preferably chloride. The reaction with acetylchloride is, for example, performed in anhydrous pyridine or in an inert solvent, e.g. anhydrous benzene, if desired in the presence of an equimolar amount of a base such as triethylamine, at temperatures ranging from room temperature to about 60° C.

Compounds of formula (V) wherein Z is —CH₂— may preferably be obtained by ring closure, under Friedel-Crafts conditions, e.g. in the presence of polyphosphoric acid, from the corresponding 2-(imidazol-2-yl)-4-phenylbutyric acids of formula (VI)

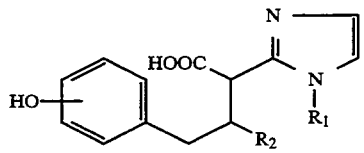

wherein R₁ and R₂ are as above defined.

Compounds (VI) may be obtained in turn from the corresponding nitriles (VII), preferably by alkaline hydrolysis, e.g. by treatment with potassium hydroxide in hydroalcoholic solution

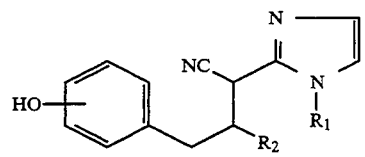

Nitriles (VII) may be obtained, e.g. by reaction in the presence of a strong base like sodium hydride in a suitable solvent, e.g. DMF or DMSO, from the corresponding 2-cyano-methylimidazoles (VIII), which are known compounds, and the appropriate phenylethylhalides of formula (IX), which are known compounds or can be easily prepared by known methods.

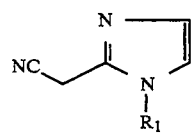

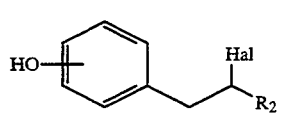

wherein Hal means halogen, e.g. chlorine or bromine, and R₁ and R₂ are as defined above.

The compounds of formula (V), wherein Z is —O—, may be for example prepared by reacting a suitable acetylsalicyl chloride with a suitable 2-methylimidazole derivative according to known procedures, e.g. as described in J. Het. Chem. 23, (1986), 1693.

PHARMACOLOGY

The compounds of the invention show inhibitory activity of the enzyme acyl CoA:cholesterol acyltransferase (ACAT-EC 2.3.1.26) which regulates the intracellular esterification of cholesterol (Suckling K. E. Stange E. F., J. Lip. Res. (1985) 26, 647) and thus the intracellular accumulation of cholesteryl esters.

The activity of this enzyme increases to the greatest extent during the atherosclerotic process in which the accumulation of esterified cholesterol in the atherosclerotic plaque is one of the predominant events (Brecher P., Chan C., B.B.A. (1980) 617. 458).

ACAT also plays a key role in the intestinal absorption of cholesterol and a significant activity of the enzyme has been observed in intestinal mucosa cells from several animal species (Heider J. G., Pickens C. E. , Kelly L. A., J. Lip. Res. (1983) 24, 1127).

By virtue of their ACAT inhibitory activity the compounds of this invention, besides having antidislipidaemic activity, act also as direct antiatherosclerotic agents, able to inhibit the development of the atheromatous plaque, and therefore may be used in particular to prevent coronary heart disease (CHD), e.g. myocardial infarction and angina. A human or animal, e.g. a mammal, may thus be treated by a method which comprises administering thereto a therapeutically effective amount of a compound of formula (I) or a pharmaceutically acceptable salt thereof. In this way the condition of the human or animal may be improved.

The activity of the enzyme and its regulation by the compounds of the invention has been evaluated in our laboratories on microsomal preparations from atherosclerotic rabbit thoracic aorta (intima media) essentially according to F. P. Bell [Atherosclerosis (1981) 38, 81]. Table 1 exemplifies the results obtained by testing for instance four representative compounds according to this invention: (+−)-5-[2-(2-phenylethyl)-3-(1-methyl-1H-imidazol-2-yl)-2H-1-benzopyran-6-yl]oxy-2,2-dimethyl-N-(2,6-diisopropylphenyl)pentanamide (internal code FCE 26734); ethyl (+−)-1-[3-(2-(2-phenylethyl)-3-(1-methyl-1H-imidazol-2-yl)-2H-1-benzopyran-6-yl)oxypropyl]cyclopentane-1-carboxylate (internal code FCE 27051); (+−)-5-[2-(2-(4-fluorophenyl)ethyl)-3-(1-methyl-1H-imidazol-2-yl)-2H-1-benzopyran-6-yl]oxy-2,2-dimethyl-N-cyclohexylpentanamide (internal code FCE 27116); (+−)-5-[2-(2-(2,4-difluorophenyl)ethyl)-3-(1-methyl-1H-imidazol-2-yl)-2H-1-benzopyran-6-yl)oxy-2,2-dimethyl-N-(2,6-diisopropylphenyl)pentanamide (internal code FCE 27113), the well known compound Bezafibrate and the prior art compound ethyl (+−)-5-[2-propyl-3-(1-methyl-1H-imidazol-2-yl)-2H-benzopyran-6-yl]oxy-2,2-dimethylpentanoate (internal code FCE 25184) which is known from WO 89/08646.

TABLE 1

| IC$_{50}$ values for the aCAT inhibition in microsomes from atherosclerotic rabbit thoracic aortas. | | |
|---|---|---|
| Compound | IC$_{50}$ (M) | limits p = 0.95 |
| FCE 26734 | $8.51 \times 10^{-8}$ | $8.15 \times 10^{-8} - 8.87 \times 10^{-8}$ |
| FCE 27051 | $6.68 \times 10^{-8}$ | $6.04 \times 10^{-8} - 7.32 \times 10^{-8}$ |
| FCE 27116 | $3.99 \times 10^{-8}$ | $1.87 \times 10^{-8} - 6.11 \times 10^{-8}$ |
| FCE 27113 | $8.22 \times 10^{-8}$ | $2.78 \times 10^{-8} - 1.37 \times 10^{-7}$ |
| FCE 25184 | $1.06 \times 10^{-6}$ | $0.77 \times 10^{-6} - 1.45 \times 10^{-6}$ |
| Bezafibrate | $5.13 \times 10^{-4}$ | $3.55 \times 10^{-4} - 8.29 \times 10^{-4}$ |

The values of IC$_{50}$ for the ACAT inhibition provide evidence that compounds of the present invention are more than 5000 times more potent than Bezafibrate, a compound whose inhibitory activity in vitro (rabbit arterial microsomes) has been already demonstrated (Hudson H., Day A., Atherosclerosis (1982) 45, 109), and more than ten times more potent than the prior art compound FCE 25184.

The dosage level suitable for oral administration to adult humans of the compounds of the invention may range from about 50 mg to about 500 mg per dose 1 to 3 times a day, depending on the disease, age and weight of the patients involved. For example, (+−)-5-[2-(2-phenylethyl)-3-(1-methyl-1H-imidazol-2-yl)-2H-1-benzopyran-6-yl]oxy-2,2-dimethyl-N-(2,6-diisopropylphenyl)pentanamide is suitably administered orally at a dose in this range.

The toxicity of the compounds of the invention is negligible, therefore they can be safely used in therapy. Nine hours food deprived mice and rats were treated orally with single administration of increasing doses, then housed and normally fed. The orientative acute toxicity (LD$_{50}$) was assessed on the seventh day after the treatment, for instance a LD$_{50}$ greater than 800 mg/kg was found in mice for the compound coded as FCE 27116.

The compounds of the invention can be administered in a variety of dosage forms, e.g. orally, in the form of tablets, capsules, sugar, or film coated tablets, liquid solutions or suspensions.

The invention includes pharmaceutical compositions comprising a compound of the invention in association with a pharmaceutically acceptable excipient (which can be a carrier or diluent).

The pharmaceutical compositions comprising the compounds of the invention are typically prepared following conventional methods and are administered in a pharmaceutically suitable form.

For example, the solid oral forms may comprise, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration may be e.g. syrups, emulsions, and suspensions. The syrups may contain as carrier, for example, saccharose or saccharose with glycerine and/or mannitol and/or sorbitol; in particular a syrup to be administered to diabetic patients can contain as carriers only products not metabolizable to glucose, or metabolizable in very small amount to glucose, for example sorbitol.

The suspensions and the emulsions may contain as carrier, for example, a natural gum, agar, sodium alginate, pectin, methylcellulose, carboxymethylcellulose, or polyvinyl alcohol. The following examples illustrate but do not limit the invention.

EXAMPLE 1

To a stirred suspension of 98 mg of sodium hydride (3.3 m mol), as a 80% dispersion in mineral oil, in anhydrous dimethylformamide (5 ml), a solution of 0.5 g of 2-(2-phenylethyl)-3-(1-methyl-1H-imidazol-2-yl)-2H-1-benzopyran-6-ol (1.64 m mol) in DMF (5 ml) is added dropwise over 5 minutes at room temperature.

After the gas evolution stops, 0.467 g of ethyl 5-bromo-2,2-dimethylpentanoate (1.97 m mol) are added in one portion and stirring is continued for 2 hours.

The reaction mixture is poured into water (70 ml), extracted with ethylacetate (3×30 ml) and the combined organic phases are washed with brine and dried over sodium sulphate. After removal of the solvent under reduced pressure, the residue is chromatographed on silica gel column (eluant n-hexane: ethyl acetate—60:40) giving 0.56 g (74%) of ethyl (+−)-5-[2-(2-phenylethyl)-3-(1-methyl-1H-imidazol-2-yl)-2H-1-benzopyran-6-yl]oxy-2,2-dimethylpentanoate light yellow oil

| ELEMENTAL ANALYSIS | | | |
|---|---|---|---|
| | C | H | N |
| found | 72.66 | 7.47 | 5.59 |
| calculated for C$_{30}$H$_{36}$N$_2$H$_4$ | 73.34 | 7.42 | 5.73 |

| $^1$H-NMR (CDCl$_3$, 200 MHz) | | | |
|---|---|---|---|
| 1.25 | 9H | m | OCH$_2$CH$_3$—C(CH$_3$)$_2$— |
| 1.70 | 4H | m | OCH$_2$CH$_2$CH$_2$ |
| 2.00 | 2H | m | CH$_2$CH$_2$ |
| 2.82 | 2H | m | CH$_2$CH$_2$Ph |
| 3.77 | 3H | s | NCH$_3$ |
| 3.89 | 2H | m | OCH$_2$CH$_2$ |
| 4.11 | 2H | q | J=7.1Hz —OCH$_2$CH$_3$ |

ELEMENTAL ANALYSIS

| 5.46 | 1H | dd | J=9.5Hz<br>J=3.8Hz | OCH |
| --- | --- | --- | --- | --- |
| 5.60–7.25 | 11H | m | aromatics  | |

By proceeding analogously the following compounds can be prepared:

ethyl (+−)-5-[2-benzyl-3-(1-methyl-1H-imidazol-2-yl)-2H-1-benzopyran-6-yl]oxy-2,2-dimethylpentanoate (light yellow oil)

ELEMENTAL ANALYSIS

|  | C | H | N |
| --- | --- | --- | --- |
| found | 72.80 | 7.30 | 5.84 |
| calculated for $C_{29}H_{34}N_2H_4$ | 73.39 | 7.22 | 5.90 |

$^1$H-NMR (CDCl$_3$, 200 MHz)

| 1.25 | 9H | m | —OCH$_2$CH$_3$—C(CH$_3$)$_2$—CO— |
| --- | --- | --- | --- |
| 1.70 | 4H | m | OCH$_2$CH$_2$CH$_2$— |
| 3.05 | 2H | m | CH$_2$Ph |
| 3.78 | 3H | s | NCH$_3$ |
| 3.92 | 2H | m | OCH$_2$—CH$_2$ |
| 4.12 | 2H | q | J=7.0Hz OCH$_2$CH$_3$ |
| 5.66 | 1H | dd | J=7.9Hz<br>J=4.9Hz OCH |
| 6.60–7.25 | 11H | m | aromatics 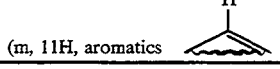 | ethyl (+−)-5-[2-(2-(4-fluorophenyl)ethyl)-3-(1-methyl-1H-imidazol-2-yl)-2H-1-benzopyran-6-yl]oxy-2,2-dimethylpentanoate light yellow oil.

ELEMENTAL ANALYSIS

|  | C | H | N | F |
| --- | --- | --- | --- | --- |
| found | 71.20 | 7.01 | 5.46 | 3.69 |
| calculated for $C_{20}H_{35}FN_2O_4$ | 71.10 | 6.96 | 5.53 | 3.75 |

$^1$H-NMR (CDCl$_3$, 200 MHz)

| 1.24 | 9H | m | —COOCH$_2$CH$_3$ —C(CH$_3$)$_2$— |
| --- | --- | --- | --- |
| 1.70 | 4H | m | OCH$_2$CH$_2$CH$_2$— |
| 2.00 | 2H | m | CH$_2$—CH$_2$—4FPh |
| 2.80 | 2H | m | CH$_2$—CH$_2$—4FPh |
| 3.78 | 3H | s | NCH$_3$ |
| 3.90 | 2H | m | OCH$_2$ |
| 4.11 | 2H | q | COOCH$_2$CH$_3$ |
| 5.43 | 1H | dd | OCH<br>J=3.5Hz<br>J=9.8Hz |
| 6.60–7.10 | 10H | m | aromatics | ethyl(+−)-1-[3-(2-(2-phenylethyl)-3-(1-methyl-1H-imidazol-2-yl)-2H-1-benzopyran-6-yl)oxypropyl]cyclopentane-1-carboxylate Low temperature melting solid

ELEMENTAL ANALYSIS

|  | C | H | N |
| --- | --- | --- | --- |
| found | 74.56 | 7.40 | 5.37 |
| calculated for $C_{32}H_{38}N_2O_4$ | 74.68 | 7.44 | 5.44 |

$^1$H-NMR (CDCl$_3$, 200 MHz)

ELEMENTAL ANALYSIS (continued)

| 1.25 | (t, J=7.1Hz, 3H, COOCH$_2$CH$_3$) |
| --- | --- |
| 1.60 | (m, 1OH, aliph.—CH$_2$—) |
| 2.10 | (m, 4H, CH$_2$CH$_2$Ph, —CH$_2$—) |
| 2.82 | (m, 2H, CH$_2$CH$_2$Ph) |
| 3.77 | (s, 3H, NCH$_3$) |
| 3.89 | (m, 2H, OCH$_2$) |
| 4.12 | (q, J=7.1Hz, 2H, COOCH$_2$) |
| 5.46 | (dd, J=3.8Hz J=9.5Hz, 1H, OCH) |
| 6.60–7.25 | (m, 11H, aromatics 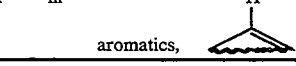) |

(+−)-6-(4,4-dimethyl-6-cyclohexyl-5-oxohexyl)oxy-2-(2-phenylethyl)-3-(1-methyl-1H-imidazol-2-yl)-2H-1-benzopyran light yellow oil

ELEMENTAL ANALYSIS

|  | C | H | N |
| --- | --- | --- | --- |
| found | 77.46 | 8.25 | 5.13 |
| calculated for $C_{35}H_{44}N_2H_2O_3$ | 77.74 | 8.20 | 5.18 |

$^1$H-NMR (CDCl$_3$, 200 MHz)

| 1.13 | 6H | s | C(CH$_3$)$_3$ |
| --- | --- | --- | --- |
| 1.42 | 1H | m | CH(cycloHex) |
| 1.63–1.77 | 14H | m | (CH$_2$)$_5$(cycloHex)<br>CH$_2$CH$_2$C(CH$_3$) |
| 2.05 | 2H | m | CH$_2$CH$_2$Ph |
| 2.46 | 2H | m | CCH$_2$<br>|<br>O |
| 2.80 | 2H | m | CH$_2$CH$_2$Ph |
| 3.76 | 3H | s | NCH$_3$ |
| 3.86 | 2H | m | OCH$_2$ |
| 5.50 | 1H | dd | J=3.7Hz J=9.5Hz OCH |
| 6.55–7.25 | 11H | m | aromatics, 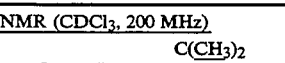 | methyl(+−)-5-[2-(2-(2,4-difluorophenyl)ethyl)-3-(1-methyl-1H-imidazol-2-yl)-2H-1-benzopyran-6-yl]oxy-2,2-dimethylpentanoate white powder m.p. 127°–129° C.

| ELEMENTAL ANALYSIS | C | H | N | F |
| --- | --- | --- | --- | --- |
| found | 67.95 | 6.31 | 5.40 | 7.50 |
| calculated for $C_{29}H_{32}F_2N_2O_4$ | 68.22 | 6.32 | 5.49 | 7.44 | ethyl(+−)-5-[2-phenylethyl)-3-(1-methyl-1H-imidazol-2-yl)-2H-1-benzopyran-7-yl]oxy-2,2-dimethylpentanoate light yellow oil

ELEMENTAL ANALYSIS

|  | C | H | N |
| --- | --- | --- | --- |
| found | 73.71 | 7.50 | 5.65 |
| calculated for $C_{30}H_{36}N_2O_4$ | 73.74 | 7.42 | 5.73 |

$^1$H-NMR (CDCl$_3$, 200 MHz)

| 1.19 | 6H | s |  | C(CH$_3$)$_2$ |
| --- | --- | --- | --- | --- |
| 1.23 | 3H | t | J=7.1Hz | COOCH$_2$CH$_3$ |
| 1.70 | 4H | m |  | OCH$_2$CH$_2$CH$_2$ |
| 1.90–2.25 | 2H | m |  | Ph CH$_2$CH$_2$ |
| 2.65–3.00 | 2H | m |  | Ph CH$_2$CH$_2$ |
| 3.75 | 1H | s |  | NCH$_3$ |
| 3.90 | 2H | m |  | OCH$_2$CH$_2$ |
| 4.11 | 2H | q | J=7.1Hz | COOCH$_2$CH$_3$ |
| 5.49 | 1H | dd | J=3.6Hz J=9.3Hz | OCH |

| ELEMENTAL ANALYSIS | | | |
|---|---|---|---|
| 6.45–7.30 | 11H | m | H aromatics  | isopropyl(+−)-5-[2-(2-phenylethyl)-3-(1-methyl-1H-imidazol-2-yl)-2H-1-benzopyran-6-yl]oxy-2,2-dimethyl-pentanoate light yellow oil

| ELEMENTAL ANALYSIS | C | H | N |
|---|---|---|---|
| found | 73.95 | 7.70 | 5.52 |
| calculated for $C_{31}H_{38}N_2O_4$ | 74.07 | 7.62 | 5.57 |

| ¹H-NMR (CDCl₃, 200 MHz) | | | |
|---|---|---|---|
| 1.18 | 6H | s | $(CH_3)_2C$ |
| 1.21 | 6H | d  J=6.3Hz | $(CH_3)_2CH$ |
| 1.70 | 4H | m | $OCH_2CH_2CH_2$ |
| 1.90–2.25 | 2H | m | $PhCH_2CH_2$ |
| 2.65–3.00 | 2H | m | $PhCH_2CH_2$ |
| 3.78 | 3H | s | $N(CH_3)$ |
| 3.90 | 2H | m | $OCH_2$ |
| 4.98 | 1H | ept. J=6.3 Hz | $(CH_3)_2CH$ |
| 5.47 | 1H | dd J=3.6Hz J=9.5Hz | $OCH$ |
| 6.55–7.25 | 11H | m | H aromatics |

(+−)-6-(4,4-dimethyl-5-oxooctyl)oxy-2-propyl-3-(1-methyl-1H-imidazol-2-yl)-2H-1-benzopyran

| ELEMENTAL ANALYSIS | C | H | N |
|---|---|---|---|
| found | 72.90 | 8.63 | 6.48 |
| calculated for $C_{26}H_{36}N_2O_3$ light yellow oil | 73.55 | 8.54 | 6.59 |

| ¹H-NMR (CDCl₃, 200 MHz) | | | |
|---|---|---|---|
| 1.90 | 6H | m | $CH_3CH_2, CH_3CH_2$ |
| 1.14 | 6H | s | $(CH_3)_2C$ |
| 1.40–1.70 | 10H | m | $OCH_2CH_2CH_2$, $CH_3CH_2CH_2CH$, $CH_3CH_2CH_2CO$ |
| 2.45 | 2H | t  J=7.1Hz | $CH_2CO$ |
| 3.85 | 2H | m | $OCH_2$ |
| 3.91 | 3H | s | $NCH_3$ |
| 5.48 | 1H | dd J=3.0Hz J=9.8Hz | $OCH$ |
| 6.60–7.25 | 6H | m | H aromatics |

(+−)-6-(4,4-dimethyl-5-oxooctyl)oxy-2-(2-phenylethyl)-3-(1-methyl-1H-imidazol-2-yl)-2H-1-benzopyran

| ELEMENTAL ANALYSIS | C | H | N |
|---|---|---|---|
| found | 75.93 | 7.90 | 5.60 |
| calculated for $C_{31}H_{38}N_2O_3$ light yellow oil | 76.51 | 7.87 | 5.75 |

| ¹H-NMR (CDCl₃, 200 MHz) | | | |
|---|---|---|---|
| 0.89 | 3H | t  J=7.3Hz | $CH_2CH_2$ |
| 1.14 | 6H | s | $(CH_3)_2C$ |
| 1.50–1.70 | 6H | m | $OCH_2CH_2CH_2$, $CH_3CH_2$ |
| 1.80–2.30 | 2H | m | $PhCH_2CH_2$ |
| 2.70–2.90 | 2H | t  J=7.2Hz | $CH_2CO$ |
| 2.80 | 2H | m | $PhCH_2CH_2$ |
| 3.75 | 3H | s | $NCH_3$ |

| ELEMENTAL ANALYSIS | | | |
|---|---|---|---|
| 3.90 | 2H | m | $OCH_2$ |
| 5.48 | 1H | dd J=3.3Hz J=9.9Hz | $OCH$ |
| 6.60–7.25 | 11H | m | H aromatics 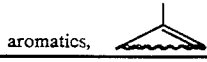 |

(+−)-1-[3-[2-(2-(4-fluorophenyl)ethyl)-3-(1-methyl-1H-imidazol-2-yl)-2H-1-benzopyran-6-yl]oxypropyl]-1-[1-oxo-2-(4-fluorophenyl)ethyl]cyclopentane;

(+−)-1-[3-[2-(2-(4-fluorophenyl)ethyl)-3-(1-methyl-1H-imidazol-2-yl)-2H-1-benzopyran-6-yl]oxypropyl]-1-(1-oxoheptyl)cyclopentane;

(+−)-7-(4,4-dimethyl-6-cyclohexyl-5-oxohexyl)oxy-2-[2-(4-fluorophenyl)ethyl]-3-(1-methyl-1H-imidazol-2-yl)-2H-1-benzopyran;

(+−)-6-[4,4-dimethyl-6-(4-fluorophenyl)-5-oxohexyl]oxy-2-[2-(4-fluorophenyl)ethyl]-3-(1-methyl-1H-imidazol-2-yl)-2H-1-benzopyran;

(+−)-6-[4,4-dimethyl-6-(2,4-dimethoxyphenyl)-5-oxohexyl]oxy-2-[2-(4-fluorophenyl)ethyl]-3-(1-methyl-1H-imidazol-2-yl)-2H-1-benzopyran;

(+−)-7-(4,4-dimethyl-6-cyclohexyl-5-oxohexyl)oxy-2-(2-phenyl-ethyl)-3-(1-methyl-1H-imidazol-2-yl)-2H-1-benzopyran;

6-(4,4-dimethyl-6-cyclohexyl-5-oxohexyl)oxy-2-(2-phenylethyl)-3-(1-methyl-1H-imidazol-2-yl)-2H-1-benzopyran, and 1-[3-[2-(2-(4-fluorophenyl)-ethyl)-3-(1-methyl-1H-imidazol-2-yl)-2H-1-benzopyran-6-yl]oxypropyl]-1-[1-oxo-2-(4-fluorophenyl)ethyl]cyclopentane.

EXAMPLE 2

A solution of 1 g (2.05 mmol) of ethyl 5-[2-(2-phenylethyl)-3-(1-methyl-1H-imidazol-2-yl)-2H-1-benzopyran-6-yl]oxy-2,2-dimethyl-pentanoate in 0.5N methanolic potassium hydroxide solution is refluxed for 5 hours.

The solvent is evaporated under vacuum and the residue taken up with water (80 ml). The aqueous solution is washed with ethyl acetate (2×60 ml) and the pH is adjusted to about 6 with 1N HCl. The precipitate is filtered, washed with ether and dried under vacuum, giving 0.54 g of 5-[2-(2-phenylethyl)-3-(1-methyl-1H-imidazol-2-yl)-2H-1-benzopyran-6-yl]oxy-2,2-dimethyl-pentanoic acid. white, powder m.p. 127°–128° C.

| ELEMENTAL ANALYSIS | C | H | N |
|---|---|---|---|
| found | 72.55 | 6.96 | 6.02 |
| calculated for $C_{28}H_{32}N_2O_4$ | 73.01 | 7.00 | 6.08 |

By proceeding analogously the following compounds can be prepared:

(+−)-1-[3-(2-(2-phenylethyl)-3-(1-methyl-1H-imidazol-2-yl)-2H-1-benzopyran-6-yl)oxypropyl]cyclopentane-1-carboxylic acid white powder m.p. 169°–171° C.

| ELEMENTAL ANALYSIS | C | H | N |
|---|---|---|---|
| found | 74.00 | 7.10 | 5.69 |
| calculated for $C_{30}H_{34}N_2O_4$ | 74.05 | 7.04 | 5.76 |

(+−)-5-[2-(2-(4-fluorophenyl)ethyl-3-(1-methyl-1H-imidazol-2-yl)-2H-1-benzopyran-6-yl]oxy-2,2-dimethylpentanoic acid white powder m.p. 140°–141° C.

| ELEMENTAL ANALYSIS | C | H | N | F |
|---|---|---|---|---|
| found | 70.20 | 6.65 | 5.80 | 4.8 |
| calculated for $C_{28}H_{31}FN_2O_4$ | 70.27 | 6.53 | 5.85 | 3.9 |

EXAMPLE 3

The acid from example 2 (1.00 g) is dissolved in 40 ml of chloroform. To this are added dropwise oxalyl chloride (0.60 ml) and DMF (0.05 ml). The resulting solution is stirred at room temperature overnight, and then concentrated under vacuum. The residue is taken up in toluene (10 ml) and slowly added to a solution of 2,6 diisopropylaniline (0.44 ml) and triethylamine (0.32 ml) in toluene (10 ml).

The resulting mixture is stirred at room temperature for four hours, is washed with water, dried, and evaporated under vacuum.

The residue is chromatographed on silica gel column (eluant n-hexane/ethyl acetate 3:2) giving 0.80 g of (+−)-5-[2-(2-phenylethyl)-3-(1-methyl-1H-imidazol-2-yl)-2H-1-benzopyran-6-yl]oxy-2,2-dimethyl-N-(2,6-diisopropyl-phenyl)pentanamide white powder m.p. 108°–110° C.

| ELEMENTAL ANALYSIS | C | H | N |
|---|---|---|---|
| found | 76.73 | 7.90 | 6.81 |
| calculated for $C_{40}H_{49}N_3O_3$ | 77.50 | 7.96 | 6.77 |

By proceeding analogously the following compounds can be prepared:

(+−)-5-[2-(2-phenylethyl)-3-(1-methyl-1H-imidazol-2-yl)-2H-1-benzopyran-6-yl]oxy-2,2-dimethyl-N-(2,4,6-trifluorophenyl)pentanamide white powder m.p. 67°–69° C.

| ELEMENTAL ANALYSIS | C | H | N | F |
|---|---|---|---|---|
| found | 69.12 | 5.91 | 7.00 | 9.75 |
| calculated for $C_{34}H_{34}F_3N_3O_3$ | 69.24 | 5.81 | 7.12 | 9.66 |

(+−)-5-[2-(2-phenylethyl)-3-(1-methyl-1H-imidazol-2-yl)-2H-1-benzopyran-6-yl]oxy-2,2-dimethyl-N-(2,4-dimethoxyphenyl)pentanamide white powder m.p. 55°–57° C.

| ELEMENTAL ANALYSIS | C | H | N |
|---|---|---|---|
| found | 72.21 | 6.98 | 6.95 |
| calculated for $C_{36}H_{41}N_3O_5$ | 72.58 | 6.93 | 7.05 |

(+−)-1-[3-[2-(2-phenylethyl)-3-(1-methyl-1H-imidazol-2-yl)-2H-1-benzopyran-6-yl]oxypropyl]cyclopentane-1-(N-2,6-diisopropylphenyl)carboxamide white powder m.p. 144°–146° C.

| ELEMENTAL ANALYSIS | C | H | N |
|---|---|---|---|
| found | 77.75 | 7.98 | 6.39 |
| calculated for $C_{42}H_{51}N_3O_3$ | 78.10 | 7.96 | 6.50 |

(+−)-1-[3-[2-(2-phenylethyl)-3-(1-methyl-1H-imidazol-2-yl)-2H-1-benzopyran-6-yl]oxypropyl]cyclopentane-1-N-cyclohexylcarboxamide white powder m.p. 88°–90° C.

| ELEMENTAL ANALYSIS | C | H | N |
|---|---|---|---|
| found | 76.00 | 7.90 | 7.30 |
| calculated for $C_{36}H_{45}N_3O_3$ | 76.15 | 7.82 | 7.27 |

(+−)-1-[3-[2-(2-(2,4-difluorophenyl)ethyl)-3-(1-methyl-1H-imidazol-2-yl)-2H-1-benzopyran-6-yl]oxypropyl]cyclopentane-1-N-(2,6-diisopropylphenyl)carboxamide white powder m.p. 111°–113° C.

| ELEMENTAL ANALYSIS | C | H | N | F |
|---|---|---|---|---|
| found | 72.58 | 7.30 | 6.10 | 5.61 |
| calculated for $C_{42}H_{49}N_3F_2O_3$ | 73.98 | 7.24 | 6.16 | 5.57 |

(+−)-5-[2-(2-(4-fluorophenyl)ethyl)-3-(1-methyl-1H-imidazol-2-yl)-2H-1-benzopyran-6-yl]oxy-2,2-dimethyl-N-isobutylpentanamide;

| ELEMENTAL ANALYSIS | C | H | N |
|---|---|---|---|
| found | 71.91 | 7.62 | 7.75 |
| calculated for $C_{32}H_{40}FN_3O_3$ light yellow low melting solid | 72.01 | 7.55 | 7.87 |

| $^1$H-NMR (CDCl$_3$, 200 MHz) | | | |
|---|---|---|---|
| 0.88 | 6H | d | J=6.7Hz | CH(CH$_3$)$_2$ |
| 1.19 | 6H | s | | C(CH$_3$)$_2$ |
| 1.70 | 4H | m | | OCH$_2$CH$_2$CH$_2$ |
| 1.90–2.20 | 2H | m | | PhCH$_2$CH$_2$ |
| 2.60–2.95 | 2H | m | | PhCH$_2$CH$_2$ |
| 3.05 | 2H | m | | CONHCH$_2$ |
| 3.78 | 3H | s | | NCH$_3$ |
| 3.87 | 2H | m | | OCH$_3$ |
| 5.41 | 1H | dd | J=3.5Hz J=9.4Hz | OCH |
| 5.70 | 1H | bt | | CONH |
| 6.55–7.10 | 10H | m | | aromatics |

(+−)-5-[2-(2-phenylethyl)-3-(1-methyl-1H-imidazol-2-yl)-2H-1-benzopyran-6-yl]oxy-2,2-dimethyl-N-(2,4,6-trimethoxyphenyl)pentanamide;

| ELEMENTAL ANALYSIS | C | H | N |
|---|---|---|---|
| found | 70.84 | 7.05 | 6.66 |
| calculated for $C_{37}H_{43}N_3O_6$ white powder m.p. 58–60° C. | 71.01 | 6.92 | 6.71 |

(+−)-5-[2-(2-(4-fluorophenyl)ethyl)-3-(1-methyl-1H-imidazol-2-yl)-2H-1-benzopyran-6-yl]oxy-2,2-dimethyl-N-(2,6-diisopropylphenyl)pentanamide;

| ELEMENTAL ANALYSIS | C | H | N | F |
|---|---|---|---|---|
| found | 75.00 | 7.54 | 6.45 | 3.06 |

-continued

| ELEMENTAL ANALYSIS | C | H | N | F |
|---|---|---|---|---|
| calculated for $C_{40}H_{48}FN_3O_3$ | 75.32 | 7.59 | 6.59 | 2.98 |
| white powder | m.p. 70–71° C. | | | |

(+ −)-5-[2-(2-(2,4-difluorophenyl)ethyl)-3-(1-methyl-1H-imidazol-2-yl)-2H-1-benzopyran-6-yl]oxy-2,2-dimethyl-N-(2,4-dimethoxyphenyl)pentanamide;

| ELEMENTAL ANALYSIS | C | H | N | F |
|---|---|---|---|---|
| found | 67.98 | 6.32 | 6.55 | 6.10 |
| calculated for $C_{36}H_{39}F_2N_3O_3$ | 68.44 | 6.22 | 6.65 | 6.01 |
| light brown powder | m.p. 51–53° C. | | | |

(+ −)-5-[2-(2-(4-fluorophenyl)ethyl-3-(1-methyl-1H-imidazol-2-yl)-2H-1-benzopyran-6-yl]oxy-2,2-dimethyl-N-cyclohexylpentanamide;

| ELEMENTAL ANALYSIS | C | H | N | F |
|---|---|---|---|---|
| found | 72.39 | 7.61 | 7.42 | 3.45 |
| calculated for $C_{34}H_{42}FN_3O_3$ | 72.95 | 7.56 | 7.50 | 3.39 |
| light brown powder | m.p. 53–55° C. | | | |

(+ −)-5-[2-(2-(2,4-difluorophenyl)ethyl)-3-(1-methyl-1H-imidazol-2-yl)-2H-1-benzopyran-6-yl]oxy-2,2-dimethyl-N-(2,6-diisopropylphenyl)pentanamide;

| ELEMENTAL ANALYSIS | C | H | N | F |
|---|---|---|---|---|
| found | 72.97 | 7.26 | 6.36 | 5.80 |
| calculated for $C_{40}H_{47}F_2N_3O_3$ | 73.25 | 7.22 | 6.41 | 5.79 |
| white powder | m.p. 69–71° C. | | | |

(+ −)-5-[2-(2-phenylethyl)-3-(1-methyl-1H-imidazol-2-yl)-2H-1-benzopyran-6-yl]oxy-2,2-dimethyl-N-cyclohexylpentanamide;

| ELEMENTAL ANALYSIS | C | H | N |
|---|---|---|---|
| found | 75.20 | 7.88 | 7.60 |
| calculated for $C_{34}H_{43}N_3O_3$ | 75.38 | 8.00 | 7.75 |
| light yellow powder | m.p. 48–50° C. dec. | | |

(+ −)-5-[2-(2(4-fluorophenyl)ethyl)-3-(1-methyl-1H-imidazol-2-yl)-2H-benzopyran-6-yl]oxy-2,2-dimethyl-N-(2,4-dimethoxyphenyl)pentanamide;

| ELEMENTAL ANALYSIS | C | H | N | F |
|---|---|---|---|---|
| found | 69.98 | 6.41 | 6.75 | 3.15 |
| calculated for $C_{36}H_{40}FN_3O_5$ | 70.45 | 6.56 | 6.84 | 3.09 |
| light brown powder | m.p. 50–52° C. | | | |

(+ −)-6-(4,4-dimethyl-5-oxooctyl)oxy-2-(2-phenylethyl)-3-(1-methyl-1H-imidazol-2-yl)-2H-1-benzopyran;
(+ −)-5-[2-(2-(4-fluorophenyl)ethyl)-3-(imidazol-2-yl)-2H-1-benzopyran-6-yl]oxy-2,2-dimethyl-N-(2,6-diisopropylphenyl)pentanamide;
(+ −)-5-[2-(2-phenylethyl)-3-(1-methyl-1H-imidazol-2-yl)-2H-1-benzopyran-7-yl]oxy-2,2-dimethyl-N-(2,6-diisopropylphenyl)pentanamide;
(+ −)-5-[2-hexyl-3-(1-methyl-1H-imidazol-2-yl)-2H-1-benzopyran-6-yl]oxy-2,2-dimethyl-N-cyclohexyl-pentanamide;
(+ −)-1-[3-[2-hexyl-3-(1-methyl-1H-imidazol-2-yl)-2H-benzopyran-6-yl]oxypropyl]cyclopentane-1-N-cyclohexylcarboxamide;
(+ −)-5-[2-hexyl-3-(1-methyl-1H-imidazol-2-yl)-2H-1-benzopyran-6-yl]oxy-2,2-dimethyl-N-hexylpentanamide;
(+ −)-5-[5,6-dihydro-6-(4-fluorophenyl)ethyl-7-(1-methyl-1H-imidazol-2-yl)naphthalen-2-yl]oxy-2,2-dimethyl-N-(2,6-diisopropylphenyl)pentanamide, and
1-[3-[5,6-dihydro-6-(4-fluorophenyl)ethyl-7-(1-methyl-1H-imidazol-2-yl)naphthalen-2-yl]oxypropyl]cyclopentane-1-N-(2,6-diisopropylphenyl)carboxamide.

EXAMPLE 4

The intermediate employed in Example 1, 2-(2-phenylethyl)-3-(1-methyl-1H-imidazol-2-yl) 2H-1-benzopyran-6-ol (m.p. 183°–185° C.), is prepared in 74% yield from the corresponding 6-methoxy-2-phenyl-3-(1-methyl-1H-imidazol-2-yl) 2H-1-benzopyran (1.7 g) by reaction with boron tribromide (18.7 m mol) in anhydrous dichloromethane.

The reaction mixture is kept at −75° C., under an inert atmosphere and than allowed to rise to 0° C. After 1 hour the reaction mixture is added with acetone and aqueous sodium bicarbonate solution and repeatedly extracted with dichloromethane.

The combined organic layer is evaporated to dryness and the residue chromatographed on silica gel column (eluant Chloroform: methyl alcohol −95:5).

By proceeding analogously similar 2-substituted 3-(1-methyl-1H-imidazol-2-yl) 2H-1-benzopyran-6-ols can be prepared. The above 6-methoxy-2-(2-phenylethyl)-3-(1-methyl-1H-imidazol-2-yl) 2H-1-benzopyran is prepared by refluxing for 2 hours a mixture of 6-methoxy-2-(2-phenylethyl)-3-(1-methyl-1H-imidazol-2-yl) 2,3-dihydro-4H-1-benzopyran-4-ol (2 g) (prepared following the procedure described in J. Het. Chem. (1984) 21, 311), phosphorous pentoxide (2 g) and Amberlite ® IR 122 (20 mg) in anhydrous benzene (200 ml).

EXAMPLE 5

With the usual methods of pharmaceutical technique, preparation can be made of capsules having the following composition:

| Composition | |
|---|---|
| (+ −)-5-[2-(2-phenylethyl)-3-(1-methyl-1H-imidazol-2–yl)–2H-1-benzopyran-6-yl]oxy-2,2-dimethyl-N-(2,6-diisopropylphenyl)pentanamide | 200 mg |
| Starch | 8 mg |
| Microcrystalline cellulose | 23 mg |
| Talc | 8 mg |
| Magnesium stearate | 5 mg. |

We claim:
1. A compound selected from:
 ethyl 5-[2-benzyl-3-(1-methyl-1H-imidazol-2-yl)-2H-1-benzopyran-6-yl]oxy-2,2-dimethylpentanoate;
 ethyl 5-[2-(2-phenylethyl)-3-(1-methyl-1H-imidazol-2-yl)-2H-1-benzopyran-6-yl]oxy-2,2-dimethylpentanoate;
 isopropyl 5-[2-(2-phenylethyl)-3-(1-methyl-1H-imidazol-2-yl)-2H-1-benzopyran-6-yl]oxy-2,2-dimethylpentanoate;

ethyl 5-[2-(2-(4-fluorophenyl)ethyl)-3-(1-methyl-1H-imidazol-2-yl)-2H-1-benzopyran-6-yl]oxy-2,2-dimethylpentanoate;

ethyl 1-[3-(2-(2-phenylethyl)-3-(1-methyl-1H-imidazol-2-yl)-2H-1-benzopyran-6-yl]oxypropyl]-cyclopentane-1-carboxylate;

ethyl 5-[2-(2-phenylethyl)-3-(1-methyl-1H-imidazol-2-yl)-2H-1-benzopyran-7-yl]oxy-2,2-dimethylpentanoate;

5-[2-(2-(4-fluorophenyl)ethyl)-3-(1-methyl-1H-imidazol-2-yl)-2H-1-benzopyran-6-yl]oxy-2,2-dimethyl-N-isobutylpentanamide;

5-[2-(2-phenylethyl)-3-(1-methyl-1H-imidazol-2-yl)-2H-1-benzopyran-6-yl]oxy-2,2-dimethyl-N-cyclohexylpentanamide;

5-[2-(2-phenylethyl)-3-(1-methyl-1H-imidazol-2-yl)-2H-1-benzopyran-6-yl]oxy-2,2-dimethyl-N-(2,4-dimethoxyphenyl)pentanamide;

5-[2-(2-phenylethyl)-3-(1-methyl-1H-imidazol-2-yl)-2H-1-benzopyran-6-yl]oxy-2,2-dimethyl-N-(2,4,6-trifluorophenyl)pentanamide;

5-[2-(2-phenylethyl)-3-(1-methyl-1H-imidazol-2-yl)-2H-1-benzopyran-6-yl]oxy-2,2-dimethyl-N-(2,4,6-trimethoxyphenyl)pentanamide;

5-[2-(2-phenylethyl)-3-(1-methyl-1H-imidazol-2-yl)-2H-1-benzopyran-6-yl]oxy-2,2-dimethyl-N-(2,6-diisopropylphenyl)pentanamide;

5-[2-(2-(4-fluorophenyl)ethyl)-3-(1-methyl-1H-imidazol-2-yl)-2H-1-benzopyran-6-yl]oxy-2,2-dimethyl-N-(2,6-diisopropylphenyl)pentanamide;

5-[2-(2-(2,4-difluorophenyl)ethyl)-3-(1-methyl-1H-imidazol-2-yl)-2H-1-benzopyran-6-yl]oxy-2,2-dimethyl-N-(2,4-dimethoxypenyl)pentanamide;

5-[2-(2-(4-fluorophenyl)ethyl)-3-(1-methyl-1H-imidazol-2-yl)-2H-1-benzopyran-6-yl]oxy-2,2-dimethyl-N-cyclohexylpentanamide;

1-[3-[2-(2-phenylethyl)-3-(1-methyl-1H-imidazol-2-yl)-2H-1-benzopyran-6-yl]oxypropyl]cyclopentane-1-N-(2,6-diisopropylphenyl)carboxamide;

1-[3-[2-(2-phenylethyl)-3-(1-methyl-1H-imidazol-2-yl)-2H-1-benzopyran-6-yl]oxypropyl]cyclopentane-1-N-cyclohexylcarboxamide;

1-[3-[2-(2-(2,4-difluorophenyl)ethyl)-3-(1-methyl-1H-imidazol-2-yl)-2H-1-benzopyran-6-yl]oxypropyl]cyclopentane-1-N-(2,6-diisopropylphenyl)carboxamide;

5-[2-(2-(2,4-difluorophenyl)ethyl)-3-(1-methyl-1H-imidazol-2-yl)-2H-1-benzopyran-6-yl]oxy-2,2-dimethyl-N-(2,6-diisopropylphenyl)pentanamide;

5-[2-(2-(4-fluorophenyl)ethyl)-3-(1-methyl-1H-imidazol-2-yl)-2H-1-benzopyran-6-yl]oxy-2,2-dimethyl-(N-(2,4-dimethoxyphenyl)pentanamide;

6-(4,4-dimethyl-5-oxooctyl)oxy-2-propyl-3-(1-methyl-1H-imidazol-2-yl)-2H-1-benzopyran;

6-(4,4-dimethyl-5-oxooctyl)oxy-2-(2-phenylethyl)-3-(1-methyl-1H-imidazol-2-yl)-2H-1-benzopyran;

6-(4,4-dimethyl-6-cyclohexyl-5-oxohexyl)oxy-2-(2-phenylethyl)-3-(1-methyl-1H-imidazol-2-yl)-2H-1-benzopyran; and methyl 5-[2-(2-(2,4-difluorophenyl)ethyl)-3-(1-methyl-1H-imidazol-2-yl)-2H-1-benzopyran-6-yl]oxy-2,2-dimethylpentanoate and the pharmaceutically acceptable salts thereof; each compound existing either as a single isomer or as a mixture of isomers thereof.

2. A pharmaceutical composition containing a suitable carrier and/or diluent and, as an active principle, a therapeutically effective amount of a compound as recited in claim 1 or a pharmaceutically acceptable salt thereof.

3. A method of treating atherosclerosis or dislipidaemia, the method comprising administering to a patient in need of such treatment a therapeutically effective amount of a compound as a recited in claim 1 or a pharmaceutically acceptable salt thereof.

4. A method of treating a patient in need of treatment with an inhibitor of the enzyme acyl CoA:cholesterol acyltransferase, the method comprising administering to said patient a therapeutically effective amount of a compound as recited in claim 1 or a pharmaceutically acceptable salt thereof.

* * * * *

UNITED STATES PATENT AND TRADEMARK OFFICE
CERTIFICATE OF CORRECTION

PATENT NO. : 5,356,920
DATED : October 18, 1994
INVENTOR(S) : Paolo COZZI et al

It is certified that error appears in the above-indentified patent and that said Letters Patent is hereby corrected as shown below:

On the Title Page, Item [75], second line, change " Severino Dino " to -- Dino Severino --.

Signed and Sealed this

Twenty-seventh Day of June, 1995

Attest:

BRUCE LEHMAN

*Attesting Officer*     *Commissioner of Patents and Trademarks*